(12) United States Patent
Carter et al.

(10) Patent No.: US 6,447,718 B1
(45) Date of Patent: Sep. 10, 2002

(54) APPARATUS AND ASSOCIATED METHOD FOR DECONTAMINATING CONTAMINATED MATTER WITH ULTRASONIC TRANSIENT CAVITATION

(75) Inventors: Stephen Douglas Carter, 1895 Chartwell Trace, Stone Mountain, GA (US) 30087; Kenneth Arthur Cunefare, Atlanta, GA (US)

(73) Assignee: Stephen Douglas Carter, Stone Mountain, GA (US)

( * ) Notice: Subject to any disclaimer, the term of this patent is extended or adjusted under 35 U.S.C. 154(b) by 0 days.

(21) Appl. No.: 09/437,358

(22) Filed: Nov. 10, 1999

(51) Int. Cl.[7] .................................................. A61L 2/00
(52) U.S. Cl. ............................ 422/20; 422/28; 422/33; 422/292; 422/295; 422/297; 422/300; 422/128; 95/30; 55/275
(58) Field of Search ............................. 422/20, 28, 33, 422/292, 295, 297, 300, 128, 1; 134/184; 366/127; 95/30; 55/279

(56) References Cited

U.S. PATENT DOCUMENTS

| | | |
|---|---|---|
| 1,711,097 A | 4/1929 | Kratzer |
| 1,728,333 A | 9/1929 | Crowther |
| 1,728,334 A | 9/1929 | Crowther |
| 3,007,478 A | 11/1961 | Leonhardt et al. |
| 3,415,613 A | 12/1968 | Wallden |
| 3,617,178 A | 11/1971 | Clouston |
| 3,627,209 A | 12/1971 | Scott |

(List continued on next page.)

FOREIGN PATENT DOCUMENTS

| | | |
|---|---|---|
| CH | 366498 | 2/1963 |
| DE | 3445990 A1 | 6/1986 |
| DE | 42 21 487 A1 | 1/1994 |
| EP | 0 040 887 A1 | 12/1981 |
| EP | 0595783 A2 * | 5/1994 |
| GB | 947699 | 1/1964 |
| GB | 2190993 | 12/1987 |

OTHER PUBLICATIONS

Cathignol, et al., "A New Shock Pressure Waveform to Amplify Transient Cavitation Effect", *IEEE Ultrasonics Symposium,* 1997, pp. 1357–1360.

Holland, et al., "Thresholds for Transient Cavitation Produced by Pulsed Ultrasound in a Controlled Nuclei Environment", *J. Accoust. Soc. Am.,* Nov. 1990, pp. 2059–2069, vol. 88, No. 5.

Boucher, R.M.G. (1979) "Ultrasonics—A Tool To Improve Biocidal Efficacy of Sterilants or Disinfectants in Hospital and Dental Practice", *Canadian Journal of Pharamaceutical Sources* 14(1)1–12.

(List continued on next page.)

*Primary Examiner*—Robert J. Warden, Sr.
*Assistant Examiner*—Imad Soubra
(74) *Attorney, Agent, or Firm*—Alston & Bird LLP

(57) ABSTRACT

An apparatus and associated method for decontaminating contaminated matter, such as an object or substance, with ultrasonic transient cavitation is disclosed. The apparatus comprises a container for containing a contaminated object, a pressure source for pressurizing the container to a predetermined pressure, a vibration source operably connected to the container, and a cleaning solution comprising a predetermined concentration of a volatile substance. The presence of the volatile substance in the cleaning solution, along with the pressurization and vibration thereof, enhances the effect of ultrasonic transient cavitation and improves decontamination of the contaminated matter. An associated method of decontaminating contaminated matter further comprises submerging the contaminated matter, such as a medical or dental instrument, in a cleaning solution having a predetermined concentration of a volatile substance, pressurizing the container, and vibrating the cleaning solution to produce ultrasonic transient cavitation therein.

27 Claims, 3 Drawing Sheets

U.S. PATENT DOCUMENTS

| | | | |
|---|---|---|---|
| 3,708,263 A | | 1/1973 | Boucher |
| 3,913,614 A | | 10/1975 | Speck |
| 3,944,387 A | | 3/1976 | Schreckendgust |
| 4,193,818 A | | 3/1980 | Young et al. |
| 4,226,642 A | | 10/1980 | Baran |
| 4,241,010 A | | 12/1980 | Baran |
| 4,543,987 A | | 10/1985 | Ekeleme, Jr. et al. |
| 4,748,003 A | | 5/1988 | Riley |
| 4,944,919 A | | 7/1990 | Powell |
| 4,973,449 A | * | 11/1990 | Kolstad et al. ............... 422/27 |
| 5,049,400 A | * | 9/1991 | Hayden ........................ 422/20 |
| 5,120,512 A | | 6/1992 | Masuda |
| 5,288,462 A | | 2/1994 | Carter et al. |
| 5,377,709 A | | 1/1995 | Shibano |
| 5,447,171 A | | 9/1995 | Shibano |
| 5,686,045 A | * | 11/1997 | Carter ......................... 422/20 |

OTHER PUBLICATIONS

Spach et al. (1993) "Transmission of Infection by Gastrointestinal Endoscopy and Bronchoscopy", American College of Physicians, *Annals of Internal Medicine* 118:117–128.

Sanchez et al. (1995) "Decontaminating Dental Instruments: Testing The Effectiveness of Selected Methods", Clinical Practice, *JADA* 126:359–368.

Hanson et al. (1992) "A Study of Glutaraldehyde Disinfection of Fibreoptic Bronchoscopes Experimentally Contaminated With *Mycobacterium Tuberculosis*", The Hospital Infection Society, *Journal of Hospital Infection* 22:137–142.

Epstein et al. (1993) "Rotary Dental Instruments and the Potential Risk of Transmission of Infection: Herpes Simplex Virus", *JADA* 124:55–59.

Epstein et al. (1995) "Assessing Viral Retention and Elimination in Rotary Dental Instruments", *JADA* 126:87–92.

* cited by examiner

1

APPARATUS AND ASSOCIATED METHOD FOR DECONTAMINATING CONTAMINATED MATTER WITH ULTRASONIC TRANSIENT CAVITATION

FIELD OF THE INVENTION

The present invention relates to an apparatus and associated method for decontaminating contaminated matter such as objects and substances and, more particularly, to a pressurizable ultrasonic cleaner having an enhanced transient cavitation effect due to the addition of a volatile substance to a cleaning solution and pressurization thereof during the ultrasonic decontamination process.

BACKGROUND OF THE INVENTION

Infection control is essential to medical and dental practices. Indeed, the Center for Disease Control, medical associations, dental associations and various states are passing laws and guidelines to increase the infection control measures that must be taken by dentists and physicians. In particular, concerns over patient to patient or staff to patient transfer of various diseases and viruses such as hepatitis B virus, HIV and other diseases have been on the rise. It is believed that most disease transfer is primarily due to the continual reuse of instruments. Therefore, efforts to combat disease transfer have generally focused on sterilizing instruments through the use of one or more of six sterilants: steam, chemical vapor, dry heat, chlorine dioxide, ethyl oxide, glutaraldehyde-containing liquid, and formaldehyde. McErlene et al., "Assessment of the Effectiveness of Dental Sterilizers Using Biological Monitors", *J. Can. Dent. Assoc.*58(6):481–83 (1992); B. Nystrom, "New Technology for Sterilization and Disinfection", Amer. *Jrl. of Med.* 91(3B):2645–2665(1991). However, the above-listed sterilants, alone and in combination, often fail to adequately, and space and cost effectively, provide a safe means for sterilization. McErlene et al., "Assessment of the Effectiveness of Dental Sterilizers Using Biological Monitors", *J. Can. Dent. Assoc.* 58(6):481–83 (1992);B. Nystrom, "New Technology for Sterilization and Disinfection", *Amer. Jrl. of Med* 91(3B):2645–65 (1991); and N. Skaug, "Proper Monitoring of Sterilization Procedures Used in Oral Surgery", *Int. J. Oral Surg.* 12:153–58 (1983).

The high percentage of sterilization ineffectiveness was highlighted in one alarming study that showed that 33% of the autoclaves used in general dental practice did not inactivate microbes. Simonsen et al., "An Evaluation of Sterilization by Autoclave in Dental Offices", *J. Dent. Res.* 58(A):Abstract No. 1236 (1979). And, in an even more alarming study of instrument sterilization procedures in oral surgery clinics, 23% of steam autoclaves; 50% of dry-heat oven sterilizers; and 100% of gas autoclaves did not kill biological spores. N. Skaug, "Proper Monitoring of Sterilization Procedures Used in Oral Surgery", *Int. J. Oral Surg.* 12:153–58 (1983).

Moreover, several other recent studies have shown that autoclave and heat sterilization routinely do not sterilize instruments. See Palenik, "Effects of Steam Sterilization on the Contents of Sharps Containers", *Am. J. Infect. Control*, 21(1):28–33 (February 1993); Palenik et al., "Effectiveness of Steam Sterilization on the Contents of Sharps Containers", *Clin. Prev. Dent.*, 14(1:28–34 (January–February 1992); B. Nystrom, "New Technology for Sterilization and Disinfection", *Am. J. Med.*, 91(3B):264S–266S (Sep. 16, 1991); and Palenik et al., "Effectiveness of Steam Autoclaving on Bacterial Endospores Placed Within Five Types of Sharp Containers Was Tested", *Am. J. Dent* 3(6)239–44 (December 1990) of dental and medical instruments are not adequately decontaminated by various combinations of presoaking agents, dishwashers, ultrasonic cleaners, detergents and water. E. Sanchez & G. MacDonald, "Decontaminating Dental Instruments: Testing the Effectiveness of Selected Method", *JADA* 126:359–68 (March, 1995). In fact, the effective sterilization of many instruments has been so unreliable that instruments are being redesigned to facilitate effective cleaning and disinfection. Spach et al., "Transmission of Infection By Gastrointestinal Endoscopy and Bronchoscopy", *Annals of Internal Medicine* 118:117–28 (1993).

In addition to inadequate sterilization equipment, problems with sterilization methods also occur because of human error. Moreover, the expense and cost of safe effective sterilization techniques may force or otherwise influence the use of less effective sterilization techniques and equipment.

When properly applied, the ultrasonic cleaning process has been shown to be beneficial for deburring and debriding various instruments and tools. Ultrasonic energy consists of vibrations or sound waves above frequencies normally heard by the human ear. Typically, an ultrasonic generator is used to produce high frequency alternating electrical currents, which are transformed into mechanical ultrasonic vibrations by a transducer. The vibrations are then transmitted into liquids consisting of either water-based or solvent-type solutions which, in turn, contact the surfaces of the object to be cleaned. Thus, the ultrasonic energy engages the object via the liquid medium to remove contaminants therefrom and/or to destroy microbial matter.

Ultrasonic cleaning increases decontamination effectiveness to a level that is difficult to achieve by other means. Over the past several years, practical ultrasonic cleaning applications have grown rapidly. For example, it is known in the art that ultrasonic transient cavitation used in conjunction with germicidal solutions will kill microbes more quickly than will a similar solution in the absence of ultrasonic transient cavitation. R. M. G. Boucher, Ph.D., "Ultrasonics—A Tool to Improve Biocidal Efficacy of Sterilants or Disinfectants in Hospital and Dental Practice", *Can. Jrl. of Pharmacology,* 17(1):1–12 (1979). However, there are currently no methods employing ultrasonic vibration as the only means of decontaminating contaminated matter such as medical or dental instruments. In current processes, instruments or objects being decontaminated are typically moved from an ultrasonic cleaning device into an autoclave for further sterilization. "Decontamination" is used herein to encompass the broadest meaning of the term and includes, for example, deburring, debriding, sterilizing, or otherwise effecting cell disruption of contaminated objects, substances, or fluids.

A need therefore exists for an apparatus and method for decontaminating contaminated matter such as dental and medical instruments that is quiet, convenient, easy to use, inexpensive, and preferably heat-independent. It would further be desirable for the apparatus and method to operate at or near room temperature such that, for example, the "cold" sterilized instruments can be rinsed, dried off and used immediately after sterilization without having to first cool down the instruments. A need further exists for an apparatus and method of improving the efficiency of ultrasonic cleaning for decontaminating contaminated matter such as medical and dental instruments such that further sterilization processes are not required for acceptable decontamination.

SUMMARY OF THE INVENTION

The above and other needs are met by the present invention which, in one embodiment, provides an apparatus for decontaminating contaminated matter comprising a pressurizable container for containing the contaminated matter, a pressure source for pressurizing the pressurizable container to a predetermined pressure, a vibration source operably connected to the pressurizable container, and a cleaning solution contained within the pressurizable container and submerging the contaminated matter. Preferably, the cleaning solution comprises a base solution and a predetermined amount of a volatile substance that is more volatile than the base solution. The cleaning solution is then pressurized by the pressure source and vibrated by the vibration source to produce ultrasonic transient cavitation therein for decontaminating the contaminated matter. The contaminated matter may comprise, for instance, medical or dental instruments, or may comprise other substances such as, for example, a fluid. Further, the pressurizable container is capable of being pressurized to greater than about 1 atmosphere, while the pressure source is capable of pressurizing the cleaning solution therein to a pressure of greater than about 1 atmosphere. Generally, the pressure to which that cleaning solution is subjected is a function of, for instance, the composition of the cleaning solution and the concentration of the added volatile substance. In some advantageous embodiments, the cleaning solution is an aqueous cleaning solution pressurized to about 2.4 atmospheres. In addition, the vibration source is capable of vibrating the cleaning solution to produce ultrasonic transient cavitation therein between the cleaning solution and the contaminated matter. Preferably, the cleaning solution comprises a base solution and a predetermined amount of a substance more volatile than the base solution, and the cleaning solution is capable of decontaminating the contaminated matter without leaving a harmful residue.

A further advantageous aspect of the present invention comprises a method for decontaminating contaminated matter, including the steps of containing a cleaning solution having a predetermined amount of a volatile substance within a pressurizable container, submerging the contaminated matter in the cleaning solution, pressurizing the cleaning solution to a predetermined pressure, and vibrating the cleaning solution to produce ultrasonic transient cavitation therein. Preferably, the pressurized cleaning solution and the presence of the volatile substance therein enhances the effect of ultrasonic transient cavitation to thereby improve decontamination of the contaminated matter. Preferably, the cleaning solution comprises a base solution and a predetermined amount of a substance more volatile than the base solution, and the cleaning solution is capable of decontaminating the contaminated matter without leaving a harmful residue. The method further comprises pressurizing the cleaning solution to a pressure of greater than about 1 atmosphere while vibrating the cleaning solution to produce ultrasonic transient cavitation therein between the cleaning solution and the contaminated matter.

Thus, embodiments of the apparatus and the method for decontaminating contaminated matter according to the present invention advantageously provide enhanced ultrasonic transient cavitation due to the addition of a volatile substance to the cleaning solution that, when pressurized and vibrated, is capable of decontaminating contaminated matter without leaving a harmful residue in a cost-effective and quiet manner while not overheating the matter being decontaminated. The ultrasonic cleaning device according to the present invention is generally convenient, easy to use, inexpensive, and operates at or near room temperature in a "cold" sterilization process which allows the matter to be utilized immediately following the sterilization process.

With the ultrasonic cleaning device according to the present invention having a pressurized cleaning solution containing a volatile substance, an enhanced and more efficient ultrasonic cleaning process is provided for decontaminating contaminated matter, such as medical and dental instruments.

DETAILED DESCRIPTION OF THE INVENTION

The present invention now will be described more fully hereinafter with reference to the accompanying drawings, in which advantageous embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
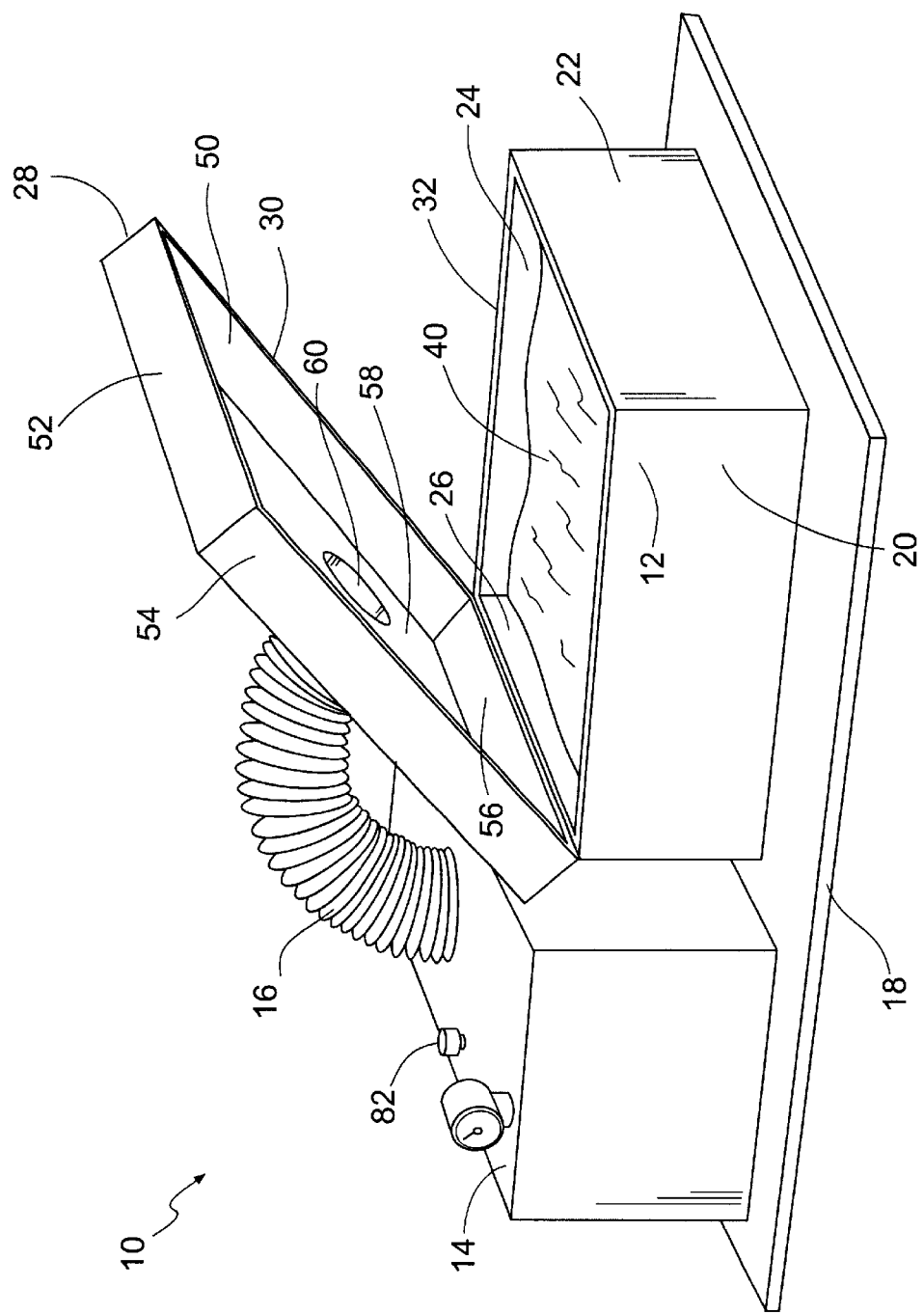
FIG. 1 is a perspective view of an apparatus for decontaminating contaminated matter according to one embodiment of the present invention.
Figure 2:
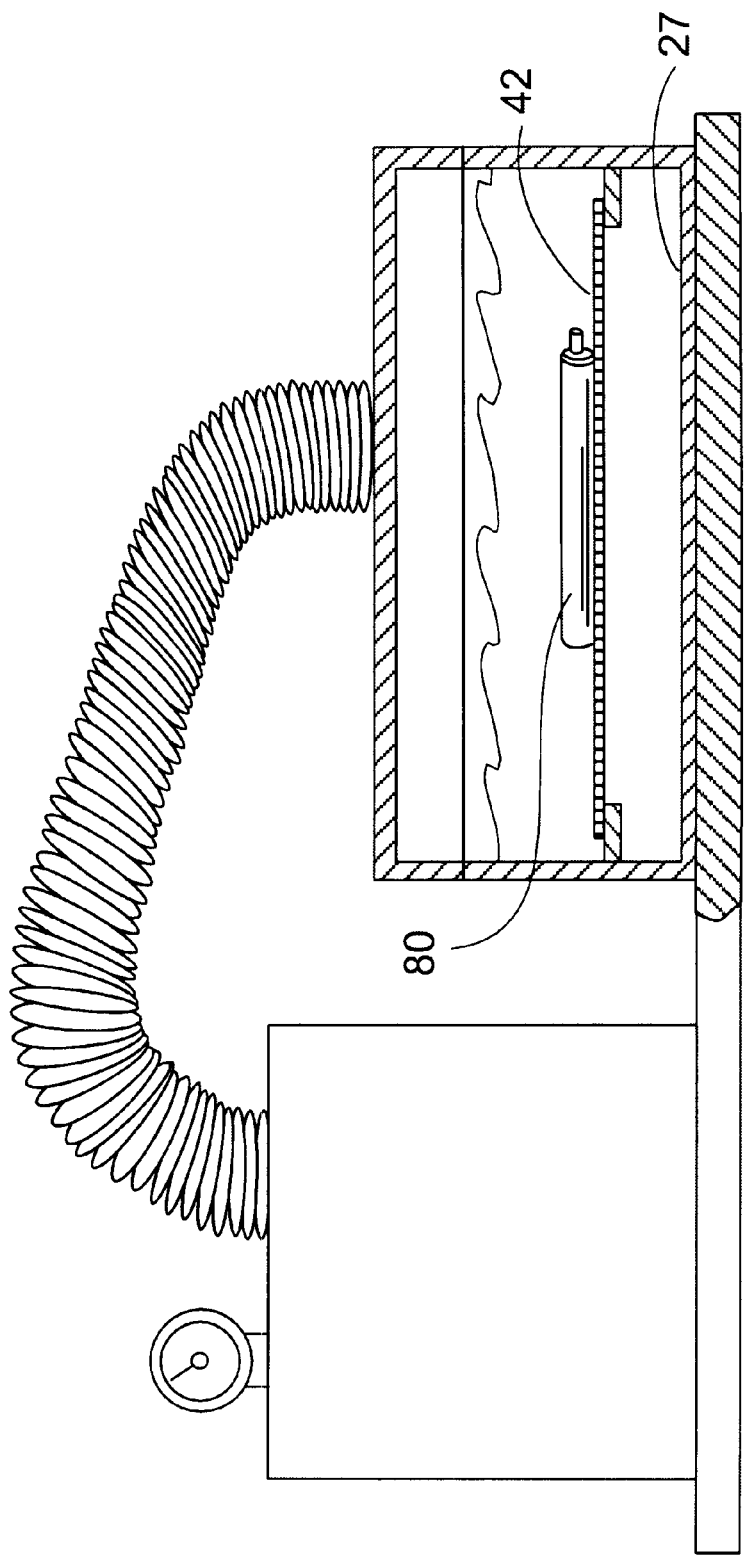
FIG. 2 is a partial side elevation of an apparatus for decontaminating contaminated matter according to one embodiment of the present invention.

As shown in FIGS. 1 and 2, one embodiment of an apparatus for decontaminating contaminated matter according to the present invention is disclosed and generally indicated by the numeral 10. The decontamination apparatus 10 comprises a pressurizable container or receptacle 12, a pressure source 14, a pressure hose 16 connecting the pressure source 14 to the receptacle 12, and a vibration source 18 operably connected to the pressurizable container 12. More particularly, the receptacle 12 generally comprises a box having multiple sidewalls 20, 22, 24, and 26 and a bottom 27. The box may be rectangularly shaped or, more generally, configured to withstand increased pressures and/or to optimize reflection/deflection of mechanical waves therein, The receptacle 12 may also include a lid 28 having multiple sides 50, 52, 54, and 56 and a top 58. The receptacle 12 is liquid-impervious such that it can contain, without leakage, a liquid cleaning solution 40. In one embodiment, where the cleaning solution is water-based, the cleaning solution 40 comprises, at least in part, a volatile substance such as, for example, isopropyl alcohol, ethyl alcohol, ether, or acetone. The volatile substance should be more volatile than the base solution, and the cleaning solution should be capable of enhancing the ultrasonic cleaning process without leaving a harmful residue on the matter being decontaminated. According to one advantageous embodiment of the present invention, the cleaning solution comprises an aqueous base solution and the volatile substance comprises isopropyl alcohol, thereby forming an aqueous cleaning solution 40 which may be between about 40% and about 99% isopropyl alcohol by volume, with the rest of the solution being water. In one particularly advantageous embodiment, an aqueous cleaning solution 40 is used which comprises about 70% by volume of isopropyl alcohol with the remainder of the solution being water.

In one embodiment, a porous support shelf 42 comprising, for example, an open grid, may be positioned inside the receptacle 12 so that a contaminated object 80, such as an instrument, can be placed on the support shelf 42. As the instrument 80 is ultrasonically cleaned, the dislodged debris falls off the instrument 80, through the porous support shelf 42, and to the bottom 27 of the receptacle 12.

The pressure source 14 may use, for example, compressed air to provide the desired pressurization of the receptacle 12 and may be any of several commonplace air compressors. For example, an Air Techniques, Incorporated compressor may be purchased from Atlanta Dental Supply Company as Model No. 230-1-60. The pressure source 14 should be capable of producing a pressure of greater than one atmosphere and, preferably, greater than about 2.4 atmospheres of pressure. The desired pressure may be dependent on a number of factors including, for instance, the composition of the cleaning solution and the concentration of the volatile substance therein. In one advantageous embodiment, the pressure source 14 is capable of producing a pressure of about 30 psi inside the receptacle 12 when the lid 28 is closed. Preferably, the pressure source 14 generates pressurized air while minimizing the temperature increase of the air as the receptacle 12 is pressurized, thereby increasing the pressure within the receptacle 12 generally independently of heat. An advantage of heat independent pressurization is that, unlike common heat-dependent sterilizers, such as autoclaves, which may release steam and/or environmental contaminants into the atmosphere upon depressurization of the receptacle 12, there is no heat or steam pressure that is released upon depressurization of the apparatus 10 according to embodiments of the present invention.

The flexible pressure hose 16 connecting the pressure source 14 to the receptacle 12 can be made of any suitable material such as plastic, metal, elastomers, textiles, or composites thereof, provided that it is able to withstand as much pressure as is necessary during the ultrasonic cleaning process according to the present invention without failure.

Operably engaging the receptacle 12 is a vibration source 18, which preferably comprises an ultrasonic generator and transducer combination that is capable of producing vibrations within the cleaning solution 40. In one advantageous embodiment, the vibration source 18 comprises an ultrasonic generator for producing high frequency alternating electrical currents and a transducer for transforming these electrical currents into mechanical ultrasonic vibrations at the desired frequency. The vibration source 18 causes ultrasonic waves in the cleaning solution 40, produces ultrasonic transient cavitation cleaning solution 40 and the instrument 80 for decontaminating the instrument 80. According to one advantageous embodiment of the present invention, the cleaning solution 40 is an aqueous cleaning solution 40 and is vibrated by the vibration source 18 at a frequency of about 24 kHz to provide an energy density in excess of bout 35 W/l therein. More generally, the vibration frequency is preferably adjustable within a range about 15 kHz and about 100 kHz, wherein the vibration frequency is adjustable to provide optimum cavitation bubble formation. In some instances, in order to minimize heating of the instruments 80 due to transient cavitation, the vibration source 18 may be cycled on and off over certain intervals of time in a "duty cycle." When a duty cycle is used in the ultrasonic cleaning process, the duration thereof may be adjusted accordingly, up to a 100% duty cycle, to meet applicable decontamination guidelines. For instance, according to one embodiment of the present invention, the vibration source 18 is operated with a duty cycle of about 10% wherein the vibration source 18 is vibrating the cleaning solution 40 for about 10% of the duration of the ultrasonic cleaning process. The term ultrasonic transient cavitation refers to transient cavitation created through the use of ultrasonic energy, wherein transient cavitation is the rapid growth of bubbles in liquids in which the bubble growth terminates in a violent, rapid collapse of the bubbles. The collapse of the bubbles is almost instantaneous and releases energy at an enormous rate. Thus, when ultrasonic transient cavitation occurs, for example, at the interface of the cleaning solution 40 and the instrument 80, the energy released by the imploding cavitation bubbles serves to deburr, debride, and/or otherwise sterilize the contaminated instrument 80. Note that this sterilization mechanism may be further capable of sterilizing other matter in addition to medical and dental instruments such as, for instance, microbially-contaminated fluids or other substances. This sterilization procedure is accomplished without overheating the solution 40 and/or the contaminated matter 80, therefore providing a "cold" sterilizing apparatus operating in a generally heat-independent matter at or near-room temperature. The above described apparatus is the subject of U.S. Pat. No. 5,686,045 to Carter et al., which is herein incorporated by reference in its entirety.

Figure 3:
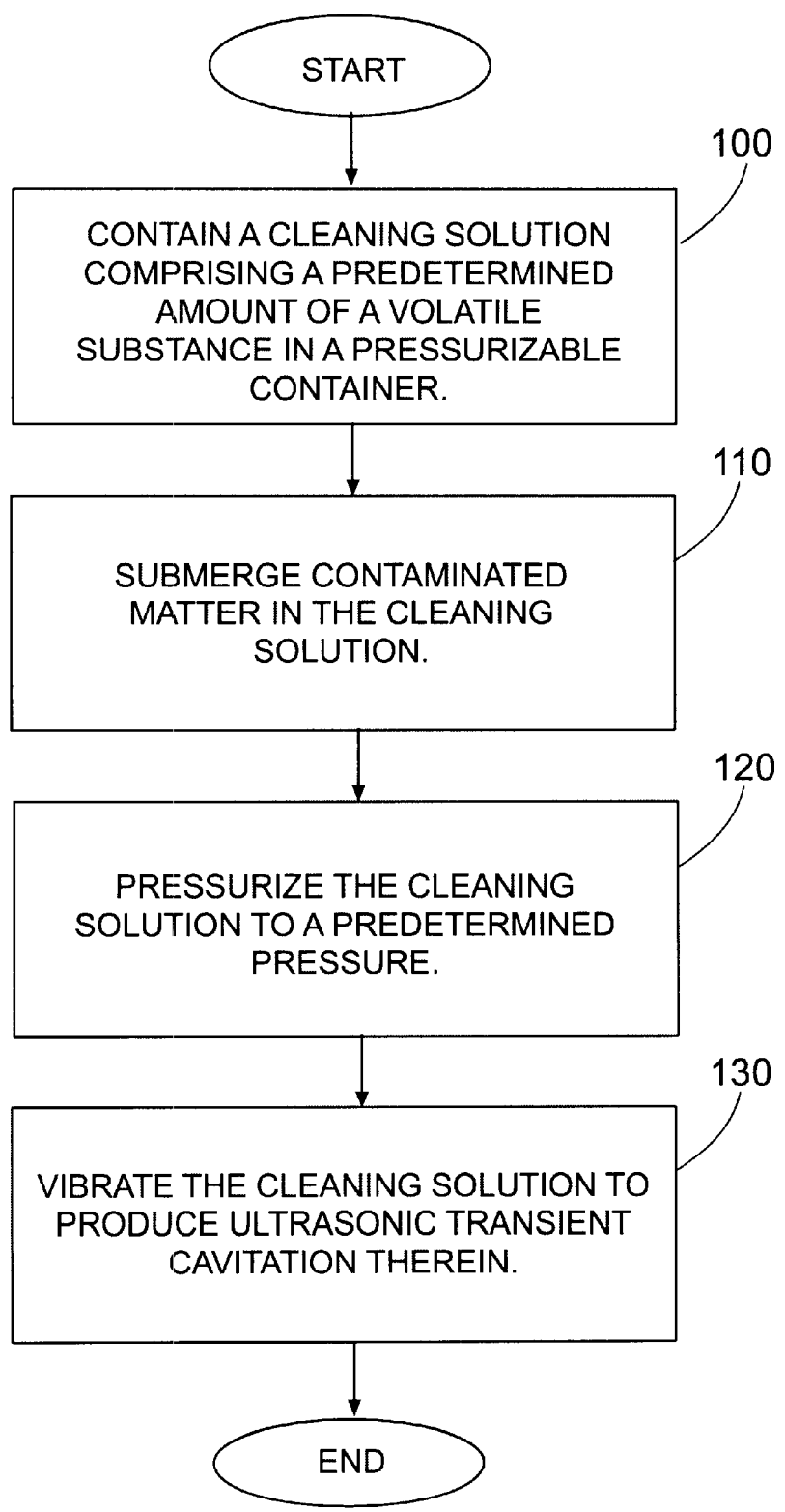
FIG. 3 is a flowchart showing a method for decontaminating contaminated matter according to one embodiment of the present invention.

A further advantageous aspect of the present invention comprises a method for decontaminating contaminated matter, as shown in FIG. 3, associated with the embodiments of the apparatus as described herein. A receptacle 12 is first filled with a cleaning solution containing, at least in part, a volatile substance 40 (block 100). The receptacle 12 is filled with the cleaning solution 40 to a level that is high enough to submerge a contaminated form of matter such as, for instance, an instrument 80, but low enough such that it will not spill over the sidewalls 20, 22, 24, and 26 of the receptacle 12. The contaminated instrument 80 is then placed within the receptacle 12 such that it is completely submerged in the cleaning solution 40 (block 110). Preferably, the cleaning solution 40 is at or near room temperature. The instrument 80 can either be placed on the bottom 27 of the receptacle 12 or it can be placed on a porous support shelf 42 disposed within the receptacle 12 and above the bottom 27. Thereafter, the lid 28 is closed such that the receptacle 12 and lid 28 are tightly sealed by the seals 30 and 32. After the lid 28 has been closed and the receptacle 12 sealed, the pressure source 14 is activated to pressurize the sealed receptacle 12 via the pressure hose 16 and lid opening 60 (block 120). The pressure within the sealed receptacle 12 is preferably generated by compressing air with minimal additional heating of the air. Most desirably, the pressure within the receptacle 12 is greater than about one atmosphere pressure and, in one advantageous embodiment, about 30 psi. After the desired amount of pressure has been generated within the sealed receptacle 12, the pressure is maintained for the duration of the ultrasonic cleaning process, until the instrument 80 is decontaminated. After the receptacle 12 is pressurized, the vibration source 18 is activated to vibrate the contents of the sealed receptacle 12 (block 130). The vibration source 18 preferably comprises arn ultrasonic generator for producing high frequency alternating electrical currents and a transducer for transforming these electrical currents into mechanical ultrasonic vibrations at the desired frequency. Most desirably, ultrasonic vibration occurs at a frequency of between about 15 kHz and about 100 kHz. In one advantageous embodiment, an aqueous cleaning solution 40 is vibrated at a frequency of about 24 kHz to provide an estimated energy density in excess of about 35 W/l.

In some instances, the duration of the ultrasonic cleaning process required for proper decontamination of the contaminated matter may be as low as one minute. However, the particular duration of the ultrasonic cleaning process required for proper decontamination of, for example, a contaminated instrument, may vary depending upon a variety of factors including, for example, the particular instrument to be decontaminated, the particular microbes contaminating the instrument, the composition of the cleaning solution, and the amount of pressure used in the cleaning process. Even though specified times for proper decontamination of the contaminated matter using ultrasonic cleaning may be provided by, for example, medical or dental guidelines, a typical procedure may involve extending the duration of the ultrasonic cleaning process for an amount of time in excess of the recommended time to ensure proper decontamination. For instance, according to one embodiment of the invention, when cleaning decontaminating common dental instruments at a pressure of about 30 psi while using isopropyl alcohol as the volatile substance in the aqueous cleaning solution, the ultrasonic cleaning process may be extended past the recommended minimum decontamination time to provide a margin of safety.

Once the ultrasonic cleaning process is complete and the instruments 80 inside the receptacle 12 are sufficiently decontaminated, the pressure within the receptacle 12 is first reduced back to atmospheric pressure by bleeding the pressure through a release valve 82 prior to opening the container lid 28. Thereafter, the lid 28 is opened and the instruments 80 are removed from the receptacle 12, rinsed, dried, and readied for use.

The enhanced ultrasonic cleaning process, using a pressurized cleaning solution comprising a volatile substance to enhance transient cavitation, is illustrated by experiments performed by Drs. Stephen Carter and Kenneth Cunefare, the inventors of the present invention, as shown in the following examples:

EXAMPLE 1

Tests were conducted utilizing various proportions of volatile substances in an aqueous cleaning solution contained within a vibratable pressurizable container to determine the effect on ultrasonic transient cavitation. A cylinder comprised of Plexiglas was utilized as the pressurizable container. A signal generator and amplifier were used to drive a piezoelectric actuator to generate the ultrasonic excitation within the aqueous cleaning solution. A test sample was suspended along the axis of the cylinder, between the plates of an integrated piezoelectric actuator and within the fluid column. Ultrasonic vibrations were then produced at a frequency of 24 kHz at a 10% duty cycle, providing an estimated energy density in excess of 35 W/l. The container was also pressurized to 30 psi during the ultrasonic cleaning process. The test sample comprised a compacted fiber spore strip and was used to demonstrate the effects of the volatile chemical concentration in the aqueous cleaning solution vis-a-vis the ultrasonic cleaning process and the increased pressure within the container. The sample was subjected to the specified energy level, vibrational frequency, and pressure for a period of ten minutes. Further, the experiment was conducted at an ambient temperature of approximately 30° C. The aqueous cleaning solution consisted of 40% isopropyl alcohol and 60% distilled water by volume. Following the ultrasonic cleaning process, the test sample showed substantial damage as manifested by visible distortion of the test sample. This damage was determined to be the result of transient cavitation. A control test was then performed on a similar test sample under the same conditions, but with an aqueous cleaning solution consisting of 100% water. Minimal effects on the physical condition of the test sample were observed.

EXAMPLE 2

Another test sample of a spore strip was subjected to the conditions described in Example 1. The aqueous cleaning solution consisted of 70% isopropyl alcohol and 30% distilled water. The test sample clearly demonstrated the effects of transient cavitation, even more so than in Example 1, as manifested by extreme and visible distortion of the test sample.

EXAMPLE 3

A further test sample of a spore strip was subjected to the conditions described in Example 1. The aqueous cleaning solution consisted of 99% isopropyl alcohol and 1% distilled water. The test sample did not show any visible distortion due to transient cavitation.

EXAMPLE 4

A test sample of dental floss was subjected to the conditions described in Example 1, except that temperature and pressure were kept at ambient levels. The aqueous cleaning solution consisted of 70% isopropyl alcohol and 30% distilled water. Though these conditions were maintained during a 45 minute ultrasonic cleaning process, the test sample did not show any visible signs of the effect of transient cavitation. However, another test sample of dental floss was then subjected to the same conditions as the previous test sample of dental floss, except at a pressure of 30 psi and for a process duration of 30 minutes. This test sample exhibited visible damage due to transient cavitation.

Thus, as illustrated by the above examples, a cleaning solution comprising isopropyl alcohol (a volatile substance) and water, combined with an elevated pressure, enhances the transient cavitational effect in an ultrasonic cleaning process. More particularly, at the same ambient temperature and under the same ultrasonic excitation conditions, test samples showed different levels of transient cavitation effects in relation to the concentration of the volatile substance in the aqueous cleaning solution and to the test pressure used. In further detail, at a pressure of 30 psi, both a 100% water and a 99% isopropyl alcohol/1% water solution exhibited negligible transient cavitation effects. A 40% isopropyl alcohol/60%l water solution showed increased transient cavitation effects as manifested in the distortion of the test sample, while a 70% isopropyl alcohol/30% water solution revealed the most severe distortion due to transient cavitation compared to the remainder of the test samples used in these experiments. With the demonstrated effect on transient cavitation of the concentration of the volatile substance in the aqueous cleaning solution 40, further, test samples were prepared and tested in a 70% isopropyl alochol/30% water solution. At ambient pressure, one test sample exhibited negligible transient cavitation effects. A second test sample was then tested in the same solution, but at a pressure of 30 psi. The second test sample exhibited visible distortion due to transient cavitation, thus demonstrating the effect of pressure on transient cavitation.

While not wishing to be bound by theory, the inventors speculate that when sufficient ultrasonic waves are introduced into a liquid, rarefactions, or low pressure areas are produced. In certain regions in the liquid, the low pressure areas transition to high pressure, or compression areas, generally at interfaces between the liquid and, for example, objects submerged therein. In water or other liquids, vapor bubbles (also known as cavitation bubbles)l frequently occur when the pressure in the liquid drops below a critical value known as the cavitation threshold. Thus, cavitation bubbles may be produced by rarefaction. The cavitation bubbles which form in the compression areas then implode during compression, wherein the pressure necessary for implosion of the cavitation bubbles may vary. Implosion of the cavitation bubbles results in the production of extremely small and localized, but highly intense, shock waves and high speed liquid jets radiating through the liquid from the point of implosion. These high intensity shock waves and high speed liquid jets then engage, for example, the surfaces of a submerged object to dislodge debris or contaminants or to neutralize microbes. Since cavitation bubble formation and implosion may take place about the object wherever the aqueous cleaning solution penetrates, such as microscopic cracks and crevices, ultrasonic cleaning is effective for even complex and intricate assemblies. The occurrence of cavitation at the interface between the liquid and the object, particularly within the crevices of the object being decontaminated, is important for providing effective decontamination. Thus, it is particularly preferred that the ultrasonic transient cavitation effect be maximized to provide optimum decontamination.

Accordingly, it is known that high vapor pressure fluids tend to produce stable cavitation bubbles which, by definition, do not tend to collapse like transient cavitation bubbles. While still not wishing to be bound by theory, the inventors further speculate that increasing vapor pressures, up to a threshold, enhances cavitation bubble formation and a bubble expansion phase that is followed by violent bubble collapse and implosion. Beyond the vapor pressure threshold, the gas volume within the cavitation bubble increases and prevents collapse thereof, therefore forming a stable cavitation bubble. For example, sea water subjected to increased pressure in the presence of sufficient ultrasonic excitation will demonstrate an increase in transient cavitation effect up to a pressure of about 2.4 atmospheres, where the implosion intensity increases in proportion to the square of the pressure, after which a further increase in pressure will reduce the magnitude of the transient cavitation effect. This is known as the Anomalous Depth Effect. T. G. Leighton, *The Acoustic Bubble,* Academic Press, 1997. The 99% isopropyl alcohol/1% water solution used in Example 3 further demonstrates the effect of a high vapor pressure fluid. As discovered, the 99% isopropyl alcohol/1% water solution exhibited a negligible transient cavitation effect on the test sample under the same test conditions which produced visible transient cavitation effects with lesser concentrated solutions. This difference is presumably the result of the high vapor pressure of 99% isopropyl alcohol/1% water solution producing stable cavitation bubbles rather than transient cavitation bubbles. Thus, according to embodiments of the present invention, when volatile substances are added in proper concentrations to pressurized cleaning solutions in an ultrasonic cleaning process, the transient cavitational effect is enhanced. This, in turn, potentiates the cleaning and antimicrobial efficacy of the ultrasonic cleaning process. The concentration of a given volatile substance added to the cleaning solution is determined by, for example, the volatility of the substance itself, the chemical compatibility of the substance with the cleaning solution, the pressure at which the process is performed, and the temperature at which the process is performed. Representative volatile substances that may be added to an aqueous cleaning solution according to embodiments of the present invention as described herein include, for example, isopropyl alcohol, ethyl alcohol, ether, and acetone. Useful volatile substances preferably include those that are more volatile than water and, preferably, effective at or near room temperature. In addition, the volatile substance should not leave a harmful residue about the matter being decontaminated and should be otherwise compatible therewith.

Various instruments may be sterilized according to embodiments of the apparatus and associated method described herein. For example, various medical instruments such as scalpels, currettes, needle holders, bone files and/or any medical instrument that is not adversely affected by increased pressures may be decontaminated according to the present invention. In addition, various dental instruments such as explorers, dressing pliers, excavators, perio probes, mirrors, handpieces and/or any dental instrument that is not adversely affected by increased pressures may also be sterilized. More generally, the apparatus and associated method disclosed herein are also capable of sterilizing heat sensitive instruments. Ultrasonic cleaning is particularly suited to sterilizing medical and dental instruments since the cleaning solution is capable of penetrating serrations, grooves, hinges, holes, cracks, crevices, interiors, and other hard to reach places of the instruments without causing damage. Heat sensitive instruments and parts thereof such as dental hand pieces, optical instruments and instruments having non-metallic parts may also be effectively sterilized by the present invention because the entire sterilization process and the associated apparatus are maintained at or near room temperature.

Thus, embodiments of the apparatus and the method for decontaminating contaminated matter according to the present invention advantageously provide enhanced ultrasonic transient cavitation due to the addition of a volatile substance to the cleaning solution that, when pressurized and vibrated, is capable of decontaminating contaminated matter without leaving a harmful residue in a cost-effective and quiet manner while generally not overheating the matter being decontaminated. The ultrasonic cleaning device according to the present invention is convenient, easy to use, inexpensive, and capable of operating at or near room temperature in a "cold" sterilization process which allows the sterilized matter to be implemented immediately following the sterilization process. With the ultrasonic cleaning device according to the present invention having a pressurized cleaning solution containing a volatile substance, an enhanced and more efficient ultrasonic cleaning technique is provided for decontaminating contaminated matter such as medical and dental instruments.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for decontaminating a contaminated object, said method comprising:

submerging the contaminated object in a cleaning solution contained within a pressurizable container;

pressurizing the pressurizable container to a predetermined pressure, greater than about 1 atmosphere, so as to pressurize the cleaning solution; and vibrating the cleaning solution at an energy density sufficient to produce ultrasonic transient cavitation, the cleaning solution comprising a base solution having a predetermined amount of a transient cavitation-enhancing substance, the transient cavitation-enhancing substance being selected so as to maximize ultrasonic transient cavitation in the cleaning solution, the maximum transient cavitation being a function of the amount of the transient cavitation-enhancing substance, the pressure, and the energy density.

2. A method according to claim 1 wherein the vibrating step further comprises vibrating the cleaning solution comprising a base solution having a predetermined amount of a volatile substance more volatile than the base solution, the cleaning solution being capable of decontaminating said contaminated object without leaving a harmful residue.

3. A method according to claim 1 wherein the vibrating step further comprises vibrating the cleaning solution comprising an aqueous base solution having a predetermined amount of a substance more volatile than water.

4. A method according to claim 1 wherein the vibrating step further comprises vibrating the cleaning solution comprising an aqueous base solution having a predetermined amount of a transient cavitation-enhancing substance selected from the group consisting of isopropyl alcohol, ethyl alcohol, ether, and acetone.

5. A method according to claim 1 wherein the vibrating step further comprises vibrating the cleaning solution comprising an aqueous base solution having between about 40 percent by volume and about 99 percent by volume of isopropyl alcohol.

6. A method according to claim 1 wherein the vibrating step further comprises vibrating the cleaning solution comprising an aqueous base solution having about 70 percent by volume of isopropyl alcohol.

7. A method according to claim 1 wherein the submerging step comprises submerging a medical instrument in the cleaning solution.

8. A method according to claim 1 wherein the submerging step comprises submerging a dental instrument in the cleaning solution.

9. A method according to claim 1 wherein the pressurizing step further comprises pressurizing the pressurizable container to a pressure of about 2.4 atmospheres.

10. A method according to claim 1 wherein the pressurizing step further comprises pressurizing the pressurizable container to a pressure of about 30 psi.

11. A method according to claim 1 wherein the vibrating step further comprises vibrating the cleaning solution to produce ultrasonic transient cavitation between the cleaning solution and the contaminated object.

12. A method according to claim 1 wherein the vibrating step further comprises vibrating the cleaning solution at a frequency of between about 15 kHz and about 100 kHz to produce ultrasonic transient cavitation between the cleaning solution and the contaminated object.

13. A method according to claim 1 wherein the vibrating step further comprises vibrating the cleaning solution at a frequency of about 24 kHz.

14. A method according to claim 1 wherein the vibrating step further comprises vibrating the cleaning solution at an energy density of greater than about 35 W/l to produce ultrasonic transient cavitation.

15. An apparatus for decontaminating a contaminated object, said apparatus comprising: a cleaning solution;
a pressurizable container for containing the contaminated object submerged in the cleaning solution;
a pressure source for pressurizing the pressurizable container to a predetermined pressure, greater than about 1 atmosphere, so as to pressurize the cleaning solution therein; and
a vibration source operably engaging the pressurizable container and configured to vibrate the cleaning solution at an energy density sufficient to produce ultrasonic transient cavitation, the cleaning solution comprising a base solution having a predetermined amount of a transient cavitation-enhancing substance, the transient cavitation-enhancing substance being selected so as to maximize ultrasonic transient cavitation in the cleaning solution, the maximum transient cavitation being a function of the amount of the transient cavitation-enhancing substance, the pressure, and the energy density.

16. An apparatus according to claim 15 wherein the pressurizable container is capable of being pressurized to greater than about 1 atmosphere.

17. An apparatus according to claim 15 wherein the pressure source is capable of pressurizing the pressurizable container to about 2.4 atmospheres.

18. An apparatus according to claim 15 wherein the pressure source is capable of pressurizing the pressurizable container to about 30 psi.

19. An apparatus according to claim 15 wherein the vibration source is capable of vibrating the cleaning solution to produce ultrasonic transient cavitation between the cleaning solution and the contaminated object.

20. An apparatus according to claim 15 wherein the vibration source is capable of vibrating the cleaning solution at a frequency of between about 15 kHz and about 100 kHz to produce ultrasonic transient cavitation between the cleaning solution and the contaminated object.

21. An apparatus according to claim 15 wherein the vibration source is capable of vibrating the cleaning solution at a frequency of about 24 kHz.

22. An apparatus according to claim 15 wherein the vibration source is capable of vibrating the cleaning solution at an energy density of greater than about 35 W/l to produce ultrasonic transient cavitation.

23. An apparatus according to claim 15 wherein the cleaning solution comprises a base solution having a predetermined amount of a substance more volatile than the base solution, the cleaning solution being capable of decontaminating the contaminated object without leaving a harmful residue.

24. An apparatus according to claim 15 wherein the cleaning solution comprises an aqueous base solution having a predetermined amount of a substance more volatile than water.

25. An apparatus according to claim 15 wherein the cleaning solution comprises an aqueous base solution having a predetermined amount of a transient cavitation-enhancing substance selected from the group consisting of isopropyl alcohol, ethyl alcohol, ether, and acetone.

26. An apparatus according to claim 15 wherein the cleaning solution comprises an aqueous base solution having between about 40 percent by volume and about 99 percent by volume of isopropyl alcohol.

27. An apparatus according to claim 15 wherein the cleaning solution comprises an aqueous base solution having about 70 percent by volume of isopropyl alcohol.

* * * * *